US006969031B2

(12) United States Patent
Ugent et al.

(10) Patent No.: US 6,969,031 B2
(45) Date of Patent: Nov. 29, 2005

(54) ADJUSTABLE MOVABLE IV STAND

(76) Inventors: Cari Lynn Ugent, 1749 N. Wells, Chicago, IL (US) 60614; Paul D. Hatch, 1308 W. Fillmore St., Chicago, IL (US) 60607; Chris K. Barmore, 703 W. Willow, #2b, Chicago, IL (US) 60614; Elizabeth Mueller, 1015 N. Elmwood Ave., Oak Park, IL (US) 60302

( * ) Notice: Subject to any disclaimer, the term of this patent is extended or adjusted under 35 U.S.C. 154(b) by 0 days.

(21) Appl. No.: 10/725,748

(22) Filed: Dec. 2, 2003

(65) Prior Publication Data

US 2005/0116126 A1    Jun. 2, 2005

(51) Int. Cl.[7] ................................................. A47F 5/00
(52) U.S. Cl. ................. 248/125.8; 248/129; 248/311.3
(58) Field of Search .......................... 248/125.3, 125.8, 248/125.1, 129, 145.6, 311.3; 5/503.1, 658

(56) References Cited

U.S. PATENT DOCUMENTS

| | | | | |
|---|---|---|---|---|
| 4,086,932 A | * | 5/1978 | Richardson | 135/67 |
| 4,725,027 A | * | 2/1988 | Bekanich | 248/125.8 |
| 4,744,536 A | * | 5/1988 | Bancalari | 248/125.8 |
| 4,892,279 A | * | 1/1990 | Lafferty et al. | 248/125.8 |
| 5,038,819 A | * | 8/1991 | Sutphen | 137/343 |
| 5,135,191 A | * | 8/1992 | Schmuhl | 248/125.1 |
| 5,421,548 A | * | 6/1995 | Bennett et al. | 248/129 |
| 5,890,687 A | * | 4/1999 | Pryor et al. | 248/158 |
| 6,224,027 B1 | * | 5/2001 | Johnson et al. | 248/125.8 |
| 6,267,613 B1 | * | 7/2001 | McCoy et al. | 439/281 |
| 6,585,206 B2 | * | 7/2003 | Metz et al. | 248/229.1 |
| 2002/0096608 A1 | * | 7/2002 | Cedarberg, III | 248/125.3 |

* cited by examiner

Primary Examiner—Ramon O Ramirez
(74) Attorney, Agent, or Firm—Katten Muchin Rosenman LLP

(57) ABSTRACT

A mobile IV pole has a wheeled base with an enclosure that substantially covers the wheels and a bumper secured to the enclosure. A pole is coupled to the base, and a plurality of hook or other holders are provided for holding intravenous fluid reservoirs. The pole may include first and second arms that extend substantially vertically upwardly from the base, each arm made up of respective lower, central, and upper telescoping tubular portions. The lower portions of the arms are securely coupled to the base, the upper portions are rigidly interconnected with one another, and the central portions of the first and second arms are rigidly interconnected by a stabilization bar which has a plurality of routing channels therein for routing flexible IV tubing. An obliquely oriented handle is coupled to the pole and is axially movable along at least a portion of the pole. The IV pole may be provided with an electrical receptacle having a retractable power cord. A hook or other hanger also may be provided at a lower portion of the pole for hanging a catheter bag, and a further hook, eyelet, or other coupling may be provided for towing the IV pole along with a gurney, wheelchair, or bed, for example.

17 Claims, 6 Drawing Sheets

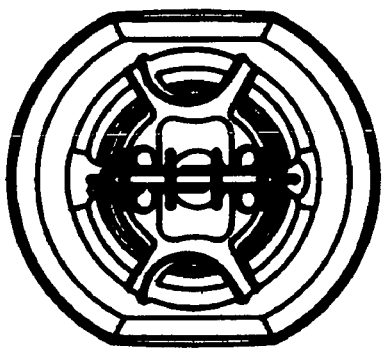
FIG. 4
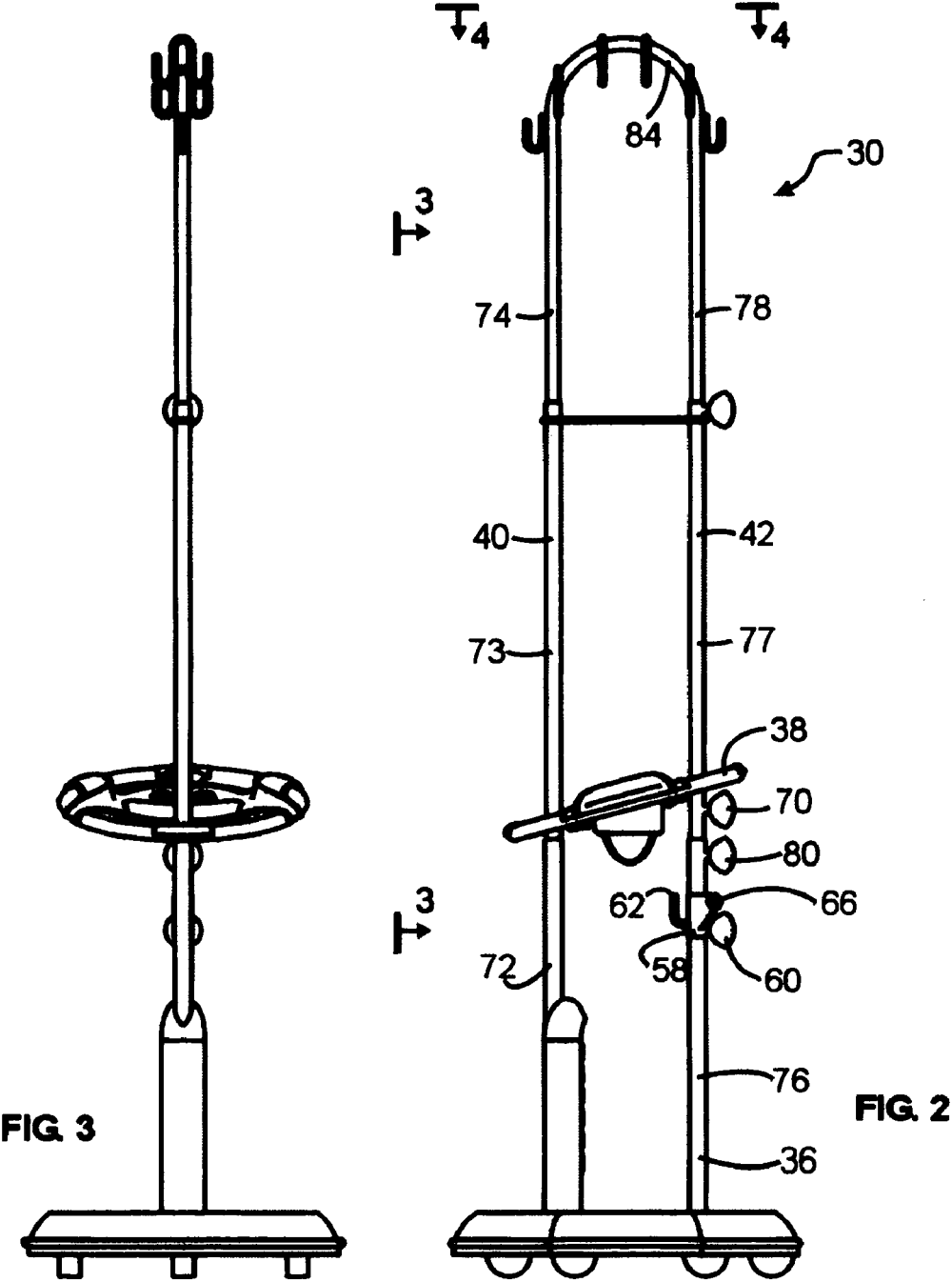
FIG. 3
FIG. 2

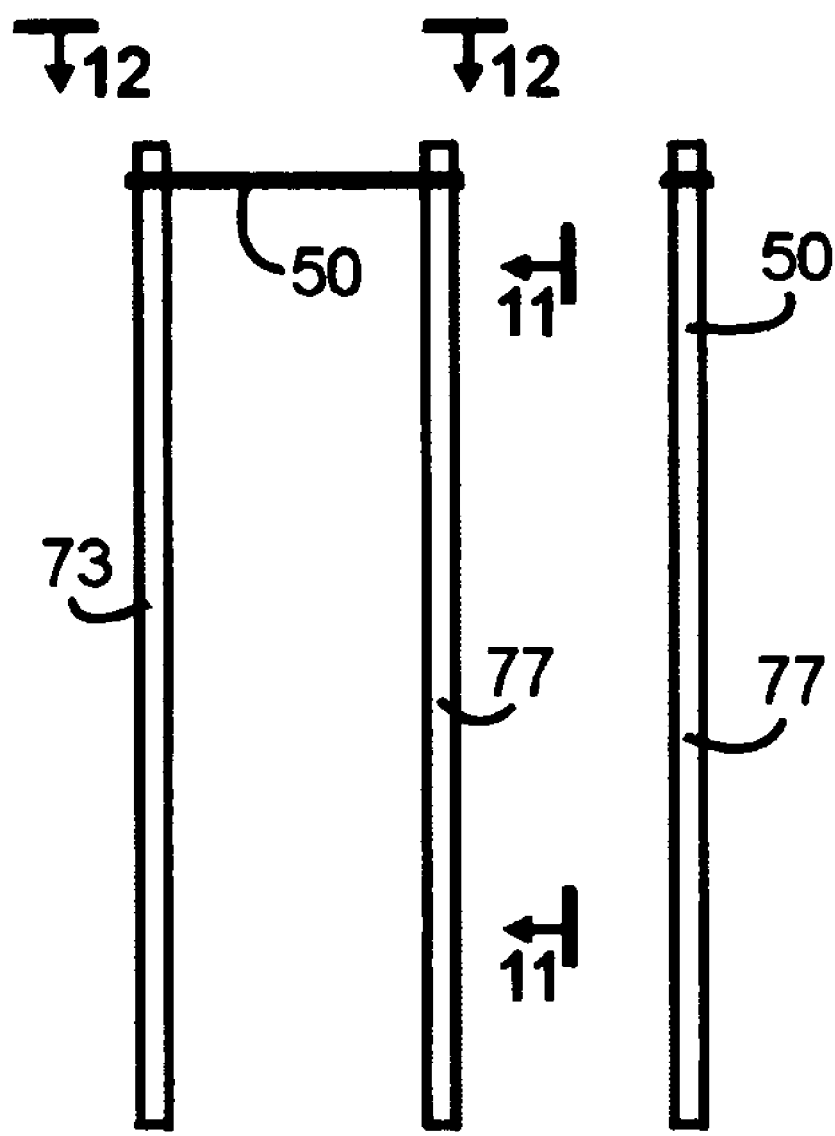

ADJUSTABLE MOVABLE IV STAND

TECHNICAL FIELD

The present invention relates generally to IV poles, and more particularly, to an IV pole including such features as an adjustable multi-height handle, an enclosed wheel base, and a retractable power cord.

BACKGROUND

For many years, patients needing intravenous fluid transfusions have been able to remain ambulatory during such transfusions by using mobile, wheeled IV poles such that the patient, while walking, can roll the IV pole alongside him or her within reach of the length(s) of flexible tubing through which intravenous fluid flows from one or more medication bags to the patient. Early mobile IV poles, however, have suffered from a number of drawbacks.

For example, prior mobile IV poles generally have not had a handle which could easily be adjusted upwardly or downwardly by a patient to accommodate patients of different heights. Prior handles also generally have been oriented horizontally such that patients could not always comfortably or safely grasp the IV pole with sufficient firmness or stability to move the IV pole while walking.

Prior mobile IV poles also typically have had exposed wheels, and many hospital patients have injured themselves by accidentally kicking or tripping over those exposed wheels while walking alongside such prior IV poles.

Several additional problems have arisen because IV poles are commonly used to carry medication pumps and other electrical equipment alongside a patient. Each such medication pump or other piece of equipment includes a power cord, which may be plugged into a conventional wall outlet to supply electricity to the medication pump or other piece of equipment. However, these power cords often become entangled or caught on other objects while the IV pole is being moved or while the patient is moving near the IV pole. This, in turn, has, in some cases, caused patients to trip and fall, or IV poles to topple, possibly resulting in injury and pain to the patient or in hazardous interruption of the patient's transfusion either because the flexible tubing is excessively strained and IV needles are pulled out of the patient, or because the power cords become unplugged from the electrical equipment and/or from the wall outlet.

Further, while newer medication pumps and other electrical equipment may have internal batteries which allow the pumps or equipment to operate for some time while unplugged, the batteries in many such devices do not provide battery-powered operation for very long. Prior IV poles have not included any additional battery or other auxiliary power supply to supplement the internal batteries of medication pumps and other electrical equipment carried by the IV pole.

In addition, conventional IV poles typically have included multiple hooks for mounting multiple medication bags for a patient. A further problem with such IV poles is that the hooks have been oriented in different directions such that the medication bags hung from such IV poles correspondingly are oriented in different directions. As a result, it becomes more difficult for a health care provider to view the medication bag labels which identify the contents of the medication bags, particularly for patients requiring a large number of contemporaneous transfusions. In addition, the lengths of flexible tubing extending from multiple medication bags hanging on an IV pole often have become crossed or entangled with one another, which also has made it more burdensome for heath care providers to distinguish one length of flexible tubing from another when connecting the tubing to the medication bags and to the patient and/or when injecting additional medications into the patient via inlets in the flexible tubing. Further, the hooks on prior IV poles generally have been mounted at a uniform height. However, various intravenous medications administered to a patient must be hung at different heights so that the medications can be delivered at particular flow rates in accordance with the patient's prescriptions. Medication bags often had to be suspended from the hooks of prior IV poles using extension hooks or other apparatus, which is cumbersome for healthcare providers and creates risk of error in the administration of various intravenous medications.

In addition to the foregoing, many patients needing IV transfusions also require urethral or other catheterization, in which a catheter (another length of flexible tubing) is connected between the patient and a catheter bag which, of course, must be maintained in close proximity to the patient. To function properly, the catheter bag must be positioned at a vertical position below the pelvis of the patient. Prior IV poles have not provided adequate means for supporting a catheter bag at a vertical position below the pelvis of the patient to ensure proper operation.

SUMMARY

The present invention relates to an IV pole which overcomes one or more of the foregoing drawbacks of prior IV poles.

According to one aspect of the present invention, an IV pole includes a base with a set of three or more wheels (e.g., six wheels) coupled thereto, a pole having a lower portion coupled to the base and an upper portion remote from the base, at least one intravenous fluid reservoir holder proximate the upper portion of the pole, and a handle coupled to the pole between the lower portion and the upper portion thereof.

According to another aspect of the present invention, an electrical receptacle may be mounted to the pole or the base of the IV pole and may include, for example, a plurality of electrical outlets. In one embodiment, the electrical receptacle comprises a six-gang plug strip.

According to another aspect of the present invention, the IV pole may be provided with a retractable power cord for electrically coupling the electrical receptacle to an electric power supply. Preferably, the retractable power cord comprises a self-coiling electric power cord.

The base of the IV pole has an enclosure that preferably substantially covers the wheels and preferably also has a bumper secured to the enclosure at an outer perimeter thereof. In one embodiment, the bumper extends along substantially the entire perimeter of the enclosure.

According to a further aspect of the invention, the handle is movable axially along at least a portion of the pole and preferably comprises a ring oriented obliquely relative to the pole. A storage receptacle optionally may be coupled to the ring.

According to yet another aspect of the present invention, the pole includes first and second arms which extend substantially vertically upwardly from the base of the IV pole. Each of the first and second arms may include a respective plurality of telescoping tubular sections. For example, each of the first and second arms may include a lower portion secured to the base, a central portion, and an upper portion. In one embodiment, the uppermost portion of the first arm is interconnected with an uppermost portion of the second arm, such as via a rigid U-shaped pole section. The respective central portions of the first and second arms may be rigidly interconnected via a stabilization bar, for example, and the stabilization bar preferably defines a plurality of routing channels sized to receive flexible tubing of the type used to carry intravenous fluid.

According to still another aspect of the invention, a fitting may be coupled to the pole proximate the base having an aperture for receiving a towing coupling, or any other suitable means for towing the IV pole may be provided.

According to yet another aspect of the invention, the IV pole also may include a hanger coupled to the pole proximate the base for hanging a catheter bag. In one embodiment, catheter bag hanger is coupled to the pole at a vertical position wherein, when a catheter bag is hung on the catheter bag hanger and coupled via a catheter to a catheterization site on a patient, the catheter bag is disposed vertically below the catheterization site on the patient.

BRIEF DESCRIPTION OF THE DRAWING

FIG. 2 is a front elevation of one exemplary embodiment of an IV pole in accordance with the present invention;

FIG. 3 is a side elevation of the IV pole of FIG. 2, viewed along the lines 3—3 therein;

FIG. 4 is a top plan view of the IV pole of FIG. 2, viewed along the lines 4—4 therein;

FIG. 10 is a fragmentary front elevation of a portion of an IV pole including a stabilization bar in accordance with the present invention;

FIG. 11 is a side elevation of the fragmentary portion shown in FIG. 10, viewed along the lines 11—11 therein; and FIG. 12 is a top plan view of the stabilization bar included in the fragmentary portion shown in FIG. 10, viewed along the lines 12—12 therein.

DETAILED DESCRIPTION

Figure 1:
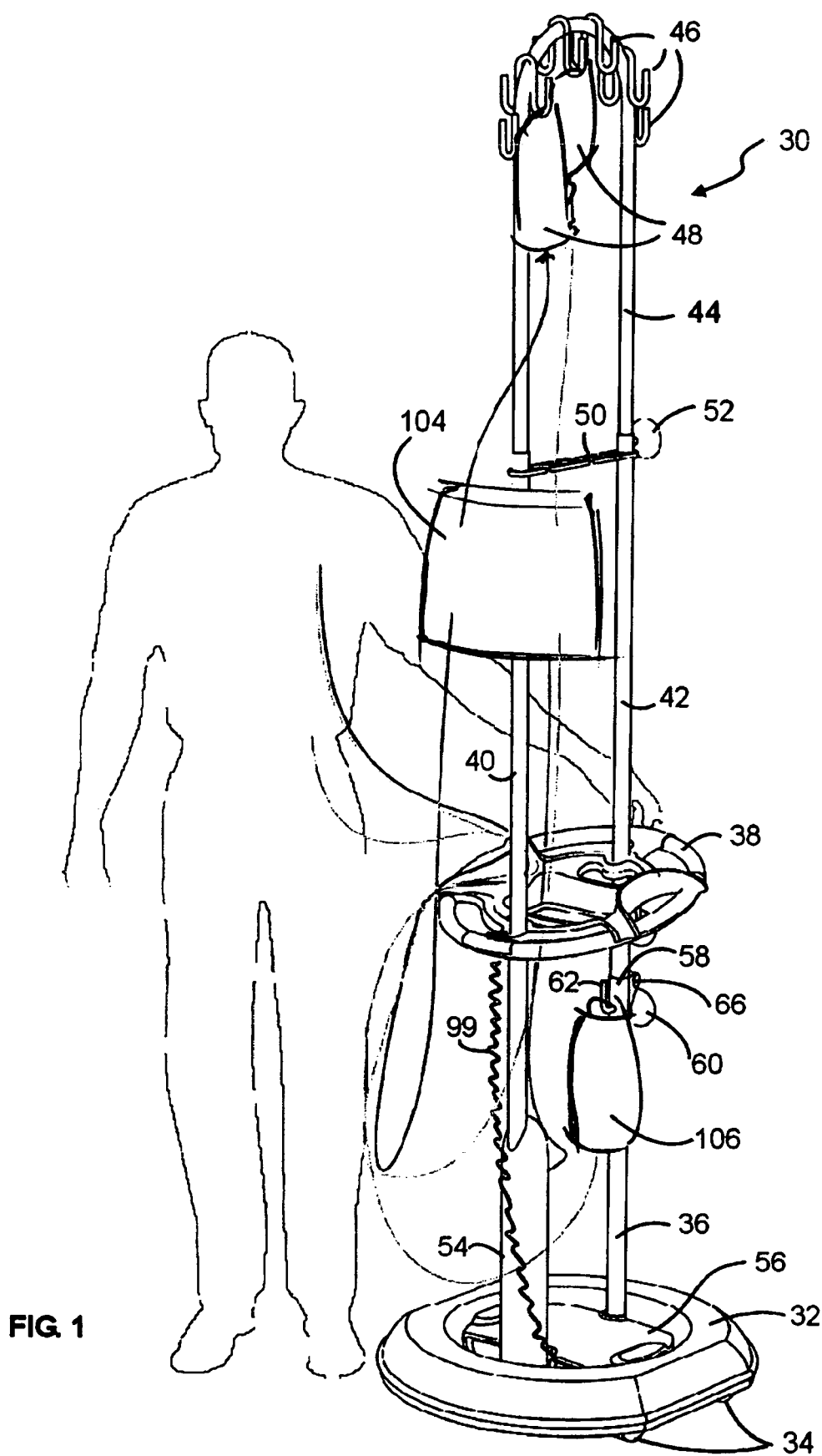
FIG. 1 depicts one exemplary embodiment of an IV pole in accordance with the present invention.

As shown in FIG. 1, an IV pole 30 includes a base 32 having a set of 3 or more wheels 34 (only two of which are visible in the view shown in FIG. 1), a pole 36 securely coupled to and extending generally upwardly from the base 32, and a handle 38 coupled to the pole 36. As illustrated in FIG. 1, the pole 36 may comprise an inverted U-shaped member having two vertical arms 40, 42 which are securely coupled to and extend generally upwardly from the base 32.

As also illustrated in FIG. 1, at an uppermost portion 44 of the pole 36, a plurality of hooks 46 or any other suitable means for holding respective intravenous fluid reservoirs 48 (e.g., IV medication bags) are provided.

A stabilization bar 50 extends laterally between and substantially rigidly interconnects the first and second arms 40, 42 relatively near the uppermost portion 44 of the pole 36. A knob 52 is provided for adjustment of the vertical height of the pole 36, and thus the altitude of the fluid reservoirs 48.

Additionally, an electrical receptacle 54 may be mounted to the pole 36 adjacent the base 32. In the illustrated embodiment, the electrical receptacle 54 is a six-gang plug strip, but any other suitable electrical receptacle could be provided instead of or in addition to the illustrated six-gang plug strip. The electrical receptacle 54 preferably includes means for receiving electric power, such as from a conventional wall outlet, and also may receive electric power from a battery 56 which, as shown in the illustrated embodiment of FIG. 1, advantageously may be received within a cavity defined by the base 32.

A collar 58 circumferentially encircles the arm 42 of the pole 36 and is axially moveable along the arm 42 (or 40), preferably proximate the base 32. A knob 60 is provided for locking the sliding collar 58 in a predetermined vertical position along the arm 42. A further hook or other hanger may be coupled to the pole proximate the base for hanging a catheter bag. In the illustrated embodiment, the hook or hanger 62 extends from the sliding collar 58 such that a catheter bag, for example, may be allowed to hang on the hook 62 proximate the lower portion 64 of the pole 36. The hook 62 or other catheter bag hanger should be coupled to the pole at a vertical position wherein, when a catheter bag is hung on the hook 62 and coupled via a catheter to a catheterization site on a patient, the catheter bag is disposed vertically below the catheterization site.

Means also may be provided for towing the IV pole 30. For example, the collar 58 additionally may define an aperture 66, which may receive a carabiner, hook, or any other towing coupling for use in tethering the IV pole 30 to a wheelchair or gurney or bed such that the IV pole 30 can be towed conveniently alongside a patient being transported with such a vehicle, or for tethering together a plurality of IV poles 30 so that they can be transported conveniently in tandem.

Additional features of an IV pole in accordance with the principles of the present invention are now described in connection with FIGS. 2–4. FIGS. 2 and 3 illustrate front and side elevations, respectively, of the IV pole 30 shown in FIG. 1, while FIG. 4 illustrates a top plan view of that IV pole as seen along the lines 4—4 in FIG. 2.

As shown in FIG. 2, the handle 38 preferably is oriented obliquely relative to the pole 36 such that, for example, as shown in FIG. 2, the handle 38 is secured at a relatively higher vertical location along the arm 42 than along the arm 40, or vice-versa. This allows the handle 38 to provide a user of the IV pole 30 with a variable-height support for holding onto and moving the IV pole 30 and for maintaining the user's balance while doing so. In addition, the overall elevation of the handle 38 above the base 32 (and thus above the ground) may be adjusted for users of different heights.

A knob 70 or other suitable means may be provided for easily adjusting the height of the handle 38. In the illustrated embodiment, the knob 70 may comprise a spring-biased peg which may be received within a plurality of apertures formed in the right arm 42 of the pole 36 at various vertical positions to vary the height of the handle 38. Alternatively, the knob 70 may comprise a screw which may be threaded into such apertures or which may instead retain the handle 38 in a desired vertical position simply by firmly tightening the screw of the knob 70 against the arm 42 itself. As will be readily appreciated by those of ordinary skill in the art, the adjustability of the height of the handle 38 may be implemented in any number of other ways in accordance with the principles of the present invention.

As also shown in FIG. 2, the arms 40 and 42 of the handle 36 may be made up of a plurality of tubular sections (e.g. the sections 72, 73, and 74 of arm 40 and the section 76, 77, and 78 of the arm 42), which preferably telescope into one another to allow the overall height of the IV pole 30 to be adjusted. In the illustrated embodiment, knobs 80 and 82 are provided to allow for easy adjustability of the height of the IV pole 30. For example, the knob 80 (which may operate in a manner similar to that described above in connection with the knob 70, for example) is provided to lock the section 77 in a predetermined axial relationship with the section 76 and to allow for adjustment of that axial relationship such that the height of the IV pole 30 can be varied. Additional adjustability is provided by a similar knob 82 which allows for adjustment of the axial relationship between the section 77 and the section 78.

In the illustrated embodiment, the uppermost portion 44 of the pole 36 is a rigid U-shaped structure including the sections 74 and 78 interconnected by a curved upper connecting portion 84, such that adjustment of the axial relationship between the section 78 and the section 77 via the knob 82 causes a corresponding adjustment of the axial relationship between the sections 74 and 73. Similarly, adjustment of the height of the IV pole 30 via the knob 80 causes an adjustment in the axial relationship between the section 73 and the section 72 which corresponds to the adjustment of the axial relationship between the sections 77 and 76. In other words, the pairs of pole sections 74, 78 and 73, 77 move together relative to one another and relative to the lowermost pair of pole sections 72, 76, which are rigidly secured to the base 32.

Figure 5:
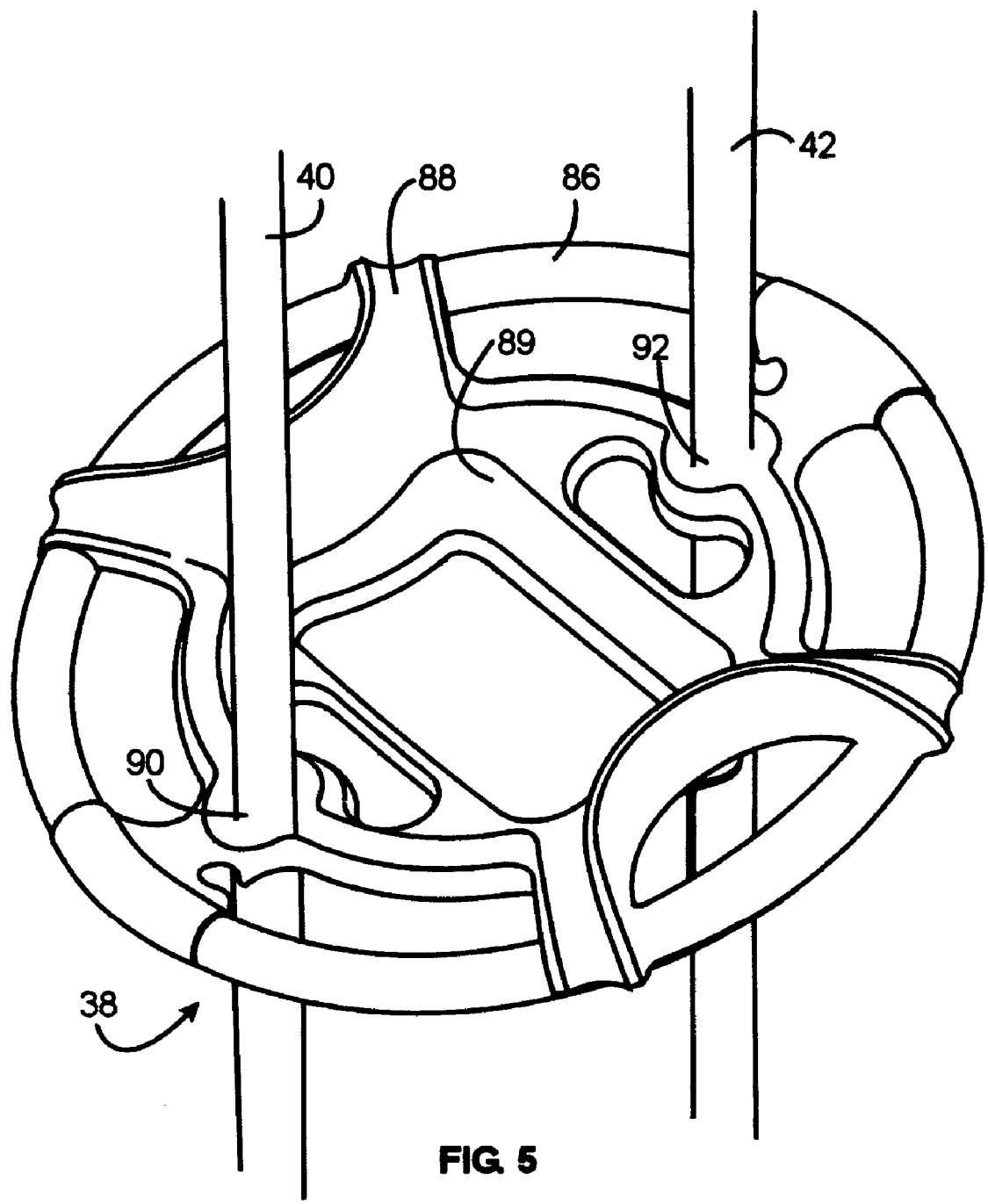
FIG. 5 depicts one exemplary embodiment of an adjustable handle for a use with an IV pole in accordance with the present invention.

FIG. 5 illustrates in greater detail one exemplary structure for the handle 38. As shown in FIG. 5, the handle 38 may include a circumferential ring 86 and a basket 88. The basket 88 may be secured to the circumferential ring 86 in any desired manner. Preferably, the basket 88 may be composed of plastic and may be vacuum-formed as a single, unitary piece. The basket 88 optionally may be reinforced with steel to provide enhanced strength. The basket 88, as shown, includes sleeves 90, 92 that can move axially upwardly and downwardly along the arms 40, 42, respectively. The sleeve 92 is provided with means (e.g., the knob 70 described above in connection with FIG. 2) for adjusting the vertical position of the basket 88, and thus the handle 38, as described above.

Preferably, as also shown in FIG. 5, the basket 88 defines several available hand positions on the circumferential ring 86 where a user can grasp the handle 38 for moving the IV pole 30 and for maintaining his or her balance while doing so. The handle also may include a storage receptacle, which may be coupled to the ring. For example, the basket 88 may define a central storage tray 89 which may be employed by a user of the IV pole 30 to carry small items while pulling or pushing the IV pole 30.

Figure 6:
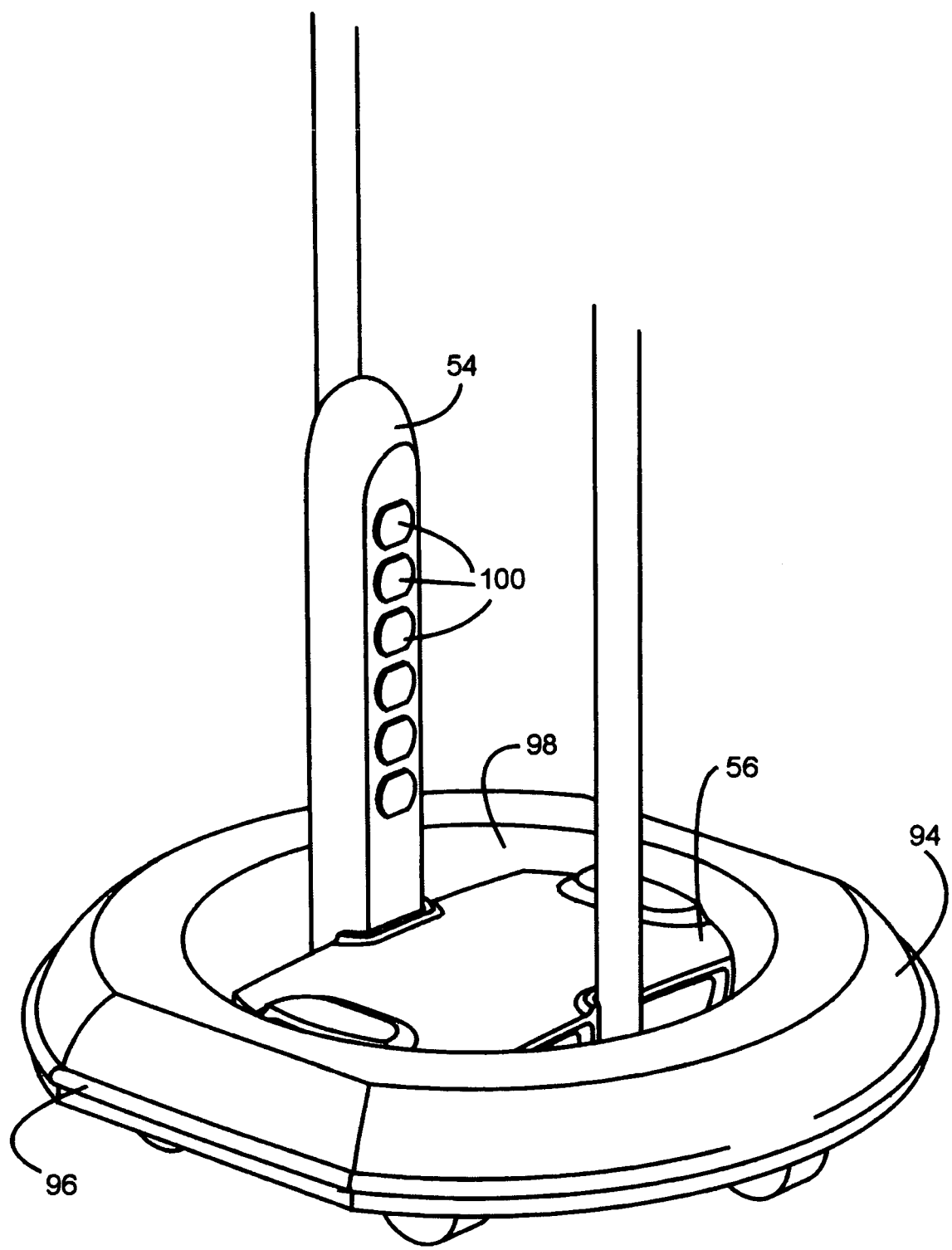
FIG. 6 depicts one exemplary embodiment of an integrated base for use with an IV pole in accordance with the present invention.

FIG. 6 illustrates one exemplary structure for the base 38 in greater detail. As shown, the base 38 may include a skirt 94, which circumferentially surrounds the set of wheels 34, which are securely coupled to the sections 72, 76 of the pole 36. Additionally, a bumper 96, preferably composed of rubber, extends circumferentially around the skirt 94 to cushion any inadvertent impact of the base 38 with walls, feet, and other obstacles. As also shown, the base defines a central cavity 98, which preferably is sized to receive a battery 56 or other suitable backup power supply, as described above. Preferably, as in the illustrated embodiment, the base comprises a unitary surface so that it is easily cleanable, unlike the more complex surface contours of bases of prior IV poles.

As also illustrated in FIG. 6, the electrical receptacle 54 preferably comprises a six-gang plug strip, which preferably is secured to the pole 36 such that the electrical outlets 100 thereon are easily accessible by a user of the IV pole 30. In addition, the electrical receptacle 54 preferably is provided with a self-coiling or otherwise retractable electrical cord 99 which, when fully extended, preferably is at least 5 feet long.

Figures 7, 8, 9:
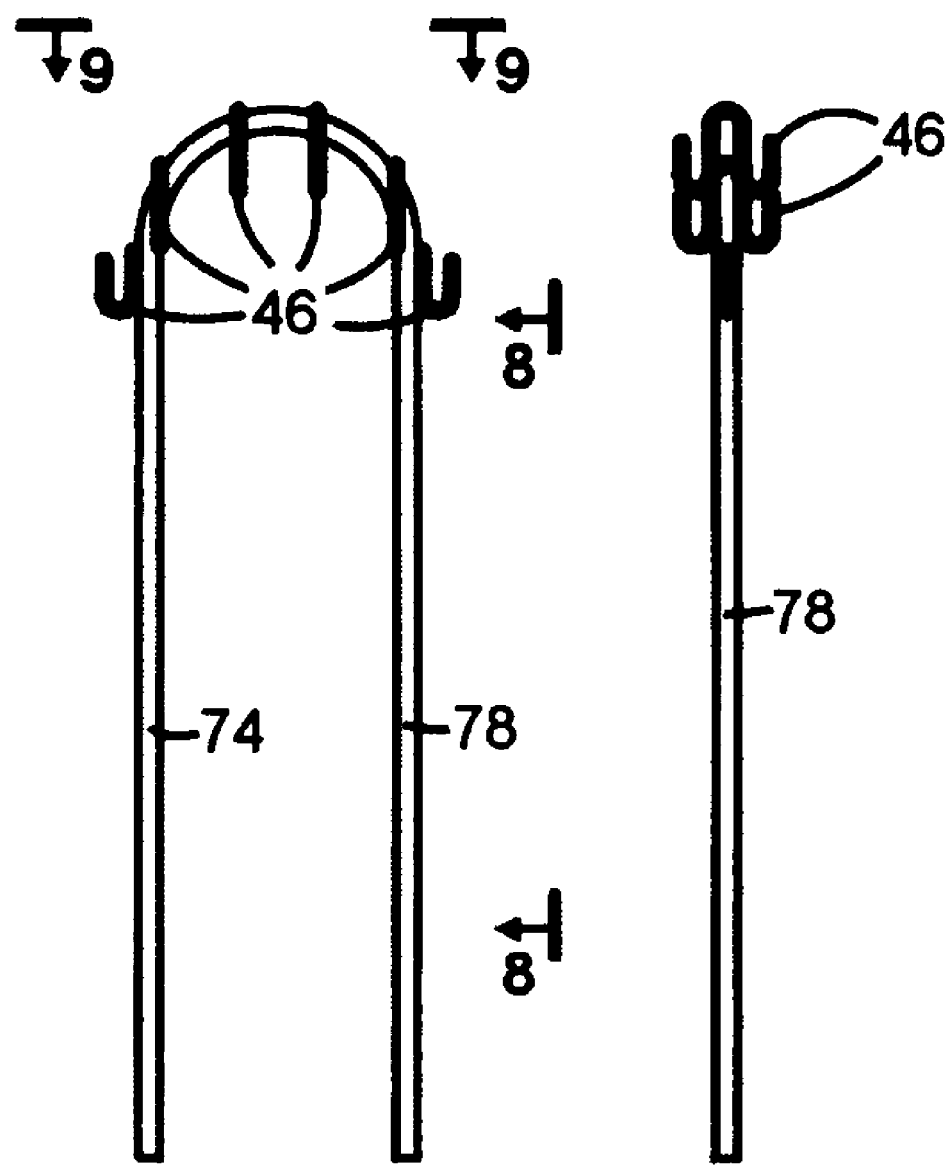
FIG. 7 is a fragmentary front elevation of an upper portion of one exemplary embodiment of an IV pole in accordance with the present invention.
FIG. 8 is a fragmentary side elevation of the fragmentary portion shown in FIG. 7, viewed along the lines 8—8 therein.
FIG. 9 is a top plan view of the fragmentary portion shown in FIG. 7, viewed along the lines 9—9 therein.

FIGS. 7, 8, and 9 illustrate various views of the uppermost portion 44 of the pole 36. As described above, the uppermost portion 44 preferably comprises an inverted U-shaped bar including tubular sections 74 and 78 interconnected by the curved upper connecting portion 84. As also shown, a plurality of hooks 46 may be secured along the curved upper connecting portion 84, spaced apart from one another and preferably oriented parallel to one another (as best shown in FIG. 9) so that intravenous fluid reservoirs (e.g., medication bags 48) may be suspended from the hooks or holders 46 and remain aligned with one another. In this way, a user of the IV pole or a medical professional administering intravenous fluid to the user may easily view the label on each respective intravenous fluid reservoir. This alignment of the medication bags 48 via the corresponding alignment of the hooks or holders 46 simplifies the task of administering medication to the patient and obviates the need for the medical professional to manipulate the medication bags 48 manually in order to view the labels identifying the contents thereof.

In addition, because the hooks 46 are mounted at various locations across the width of the curved upper connecting portion 84 of the the inverted U-shaped bar, the heights of the various hooks 46 is vertically staggered so that various intravenous medications to be administered to a patient can be hung from higher or lower hooks 46 depending upon the flow rate at which the medications must be administered to the patient. Thus, the hooks 46 serve to align the medication bags 48 and also to allow them to be hung at staggered heights so that various intravenous infusions can run simultaneously without any need for cumbersome extension or "piggy-back" hooks. This design further facilitates simultaneous viewing of the labels of all medication bags 48, because each medication bag 48 may be hung from its own hook 46 and no two medication bags 48 will need to be linked or piggy-backed together.

Similarly, FIGS. 10, 11, and 12 depict in greater detail the pole sections 73, 77 and the stabilization bar 50 that interconnects them. Preferably the sections 73 and 77 are substantially rigidly coupled together via the stabilization bar 50 such that movement of, for example, section 77 relative to section 76 produces, as described above, produces a corresponding movement of section 73 relative to section 72.

FIG. 12 shows a top plan view of the structure shown in FIG. 10 and particularly illustrates the profile of the stabilization bar 50. As shown, in addition to interconnecting the tubular sections 73 and 77, the stabilization bar 50 may be shared to define a plurality of routing channels 102 which may be used to route and organize the lengths of flexible tubing used to deliver intravenous fluid from medication bags 48 suspended from the hooks 46 to a patient. Thus, the routing channels 102 in the stabilization bar 50 aid in reducing entanglement of the various lengths of flexible tubing extending from the medication bags 48.

As shown in FIG. 1 conventional electronic medication pump 104 may be mounted to the pole 36 as shown in FIG. 1 and flexible tubing may be routed from a medication bag 48 through a routing channel 102 in the stabilization bar 50 to the medication pump 104, which, in turn, pumps the fluid from the medication bag 48 through a further length of flexible tubing to the patient. As will be evident to those of ordinary skill in the art, additional medication bags 48 and electronic medication pumps 104 may be secured to the IV pole 30 in accordance with the medical needs of any particular patient. An advantage of the IV pole 30 is that the two arms 40, 42 of the pole 36 can accommodate a larger number of medication pumps 104 and other equipment than prior single-arm IV poles. The two-arm design of the pole 36 also provides space on the IV pole 30 for multiple compressed gas canisters to be transported with a patient who may require supplemental oxygen for respiration, for example.

In addition, for a patient who requires urethral or other catheterization, a catheter from the patient may be connected to a catheter bag 106 (FIG. 1), which may be hung from the hook 62 at a vertical position on the pole 36 generally below the pelvis of the patient. Each of the electronic medication pumps 104 may be conveniently plugged into the electrical receptacle 54, and the self-coiling or retractable cord 99 thereof may then be plugged into a wall outlet to supply electric power conveniently to all of the medication pumps. As a result, only one cord must be plugged in to power the medication pumps, and only one cord extends from the IV pole 30 to the wall outlet (namely, the self-coiling or retractable power cord 99).

The foregoing description is for the purpose of teaching those skilled in the art the best mode of carrying out the invention and is to be construed as illustrative only. Numerous modifications and alternative embodiments of the invention will be apparent to those skilled in the art in view of this description, and the details of the disclosed structure may be varied substantially without departing from the spirit of the invention. Accordingly, the exclusive use of all modifications within the scope of the appended claims is reserved.

What is claimed is:

1. An IV pole, comprising:
    a base with a set of three or more wheels coupled thereto, wherein the base comprises an enclosure that substantially covers and substantially circumferentially surrounds and encloses the set of wheels;
    a pole having a lower portion coupled to the base and an upper portion remote from the base;
    at least one intravenous fluid reservoir holder proximate the upper portion of the pole; and
    a handle coupled to the pole between the lower portion and the upper portion thereof.

2. The IV pole of claim 1, further comprising a bumper secured to the enclosure at an outer perimeter thereof.

3. The IV pole of claim 2, wherein the bumper extends along substantially the entire perimeter of the enclosure.

4. The IV pole of claim 1, wherein the set of wheels comprises six wheels.

5. The IV pole of claim 1, further comprising a bumper secured to the base at an outer perimeter thereof.

6. The IV pole of claim 5, wherein the bumper extends along substantially the entire perimeter of the base.

7. An IV pole, comprising:
    a base with a set of three or more wheels coupled thereto;
    a pole having a lower portion coupled to the base and an upper portion remote from the base;
    at least one intravenous fluid reservoir holder proximate the upper portion of the pole; and
    a handle coupled to the pole between the lower portion and the upper portion thereof, wherein the handle comprises a ring oriented obliquely relative to the pole.

8. The IV pole of claim 7, wherein the handle is movable axially along at least a portion of the pole.

9. The IV pole of claim 7, wherein the handle further comprises a storage receptacle coupled to the ring.

10. An IV pole, comprising:
    a base with a set of three or more wheels coupled thereto;
    a pole having a lower portion coupled to the base and an upper portion remote from the base, wherein the pole comprises a first arm extending substantially vertically upwardly from a first portion of the base and a second arm extending substantially vertically upwardly from a second portion of the base different than the first portion;
    at least one intravenous fluid reservoir holder proximate the upper portion of the pole; and
    a handle coupled to the pole between the lower portion and she upper portion thereof.

11. The IV pole of claim 10, wherein an uppermost portion of the first arm is interconnected with an uppermost portion of the second arm via a rigid U-shaped pole section.

12. The IV pole of claim 10, wherein each of the first and second arms comprises a respective plurality of telescoping tubular sections.

13. The IV pole of claim 10, wherein each of the first and second arms comprises a lower portion secured to the base, a central portion, and an upper portion.

14. The IV pole of claim 13, wherein the upper portion of the first arm is interconnected with the upper portion of the second arm.

15. The IV pole of claim 14, wherein the central portions of the first and second arms are rigidly interconnected via a stabilization bar.

16. The IV pole of claim 15, wherein the stabilization bar defines a plurality of routing channels sized to receive flexible tubing used to carry intravenous fluid.

17. An IV pole, comprising:
    a base with a set of at least three wheels coupled thereto, wherein the base includes an enclosure that substantially covers the wheels and a bumper secured to the enclosure at an outer perimeter thereof;
    a pole comprising first and second arms extending substantially vertically upwardly from the base, each arm comprising respective lower, central, and upper telescoping portions, wherein the respective lower portions of the first and second arms are securely coupled to the base, and wherein the respective upper portions of the first and second arms are rigidly interconnected with one another, and wherein the respective central portions of the first and second arms are rigidly interconnected via a stabilization bar having a plurality of routing channels sized to receive flexible tubing;
    at least one intravenous fluid reservoir holder mounted to the pole proximate the uppermost end thereof; and
    a handle coupled to the pole and movable axially along at least a portion of the pole, wherein the handle comprises a ring oriented obliquely relative to the pole.

* * * * *